United States Patent
Bar-Tal et al.

(10) Patent No.: US 10,307,078 B2
(45) Date of Patent: Jun. 4, 2019

(54) TRAINING OF IMPEDANCE BASED LOCATION SYSTEM USING REGISTERED CATHETER IMAGES

(71) Applicant: BIOSENSE WEBSTER (ISRAEL) LTD., Yokneam (IL)

(72) Inventors: Meir Bar-Tal, Haifa (IL); Doron Moshe Ludwin, Haifa (IL)

(73) Assignee: BIOSENSE WEBSTER (ISRAEL) LTD, Yokeam (IL)

( * ) Notice: Subject to any disclaimer, the term of this patent is extended or adjusted under 35 U.S.C. 154(b) by 345 days.

(21) Appl. No.: 14/621,581

(22) Filed: Feb. 13, 2015

(65) Prior Publication Data

US 2016/0235339 A1  Aug. 18, 2016

(51) Int. Cl.
*A61B 6/00* (2006.01)
*A61B 5/06* (2006.01)
(Continued)

(52) U.S. Cl.
CPC ............. *A61B 5/063* (2013.01); *A61B 5/042* (2013.01); *A61B 5/04012* (2013.01); *A61B 5/062* (2013.01); *A61B 5/066* (2013.01); *A61B 5/0816* (2013.01); *A61B 5/6852* (2013.01); *A61B 6/12* (2013.01); *A61B 5/0538* (2013.01); *A61B 5/6823* (2013.01); *A61B 2034/2051* (2016.02); *A61B 2576/023* (2013.01)

(58) Field of Classification Search
None
See application file for complete search history.

(56) References Cited

U.S. PATENT DOCUMENTS 5,274,551 A   12/1993  Corby, Jr.
5,546,951 A   8/1996   Ben Haim
(Continued)

FOREIGN PATENT DOCUMENTS

EP   1658818 A1   5/2006
EP   2168478      3/2010
(Continued)

OTHER PUBLICATIONS

Landau, L.D. et al., Electrodynamics of Continuous Media. Pergamon Press (1960) vol. 8, Sec. 45., pp. 189-190. of Course of Theoretical Physics, Textbook: ISBN No. 0-08-09105-9.
(Continued)

*Primary Examiner* — Jonathan Cwern
(74) *Attorney, Agent, or Firm* — Louis J. Capezzuto

(57) ABSTRACT

A method, including inserting a catheter having at least one electrode into a chamber of a body organ of a patient and recording at a sequence of times respective sets of currents between the at least one electrode and a plurality of patches positioned on skin of the patient. The method further includes, while recording the sets of currents, acquiring x-ray images of the at least one electrode, and determining locations of the catheter from the images. A relation is derived between the locations and the respective sets of currents based on the sets of currents and the images. The method also includes recording subsequent sets of currents between the at least one electrode and the patches, and determining, based on the relation, subsequent locations of the catheter in response to the subsequent set of currents.

19 Claims, 5 Drawing Sheets

(51) Int. Cl.
*A61B 6/12* (2006.01)
*A61B 5/04* (2006.01)
*A61B 5/042* (2006.01)
*A61B 5/08* (2006.01)
*A61B 5/00* (2006.01)
A61B 34/20 (2016.01)
A61B 5/053 (2006.01)

(56) References Cited

U.S. PATENT DOCUMENTS

| | | | |
|---|---|---|---|
| 5,738,096 A | 4/1998 | Ben Haim | |
| 6,147,480 A | 11/2000 | Osadchy et al. | |
| 6,226,542 B1 | 5/2001 | Reisfeld | |
| 6,301,496 B1 | 10/2001 | Reisfeld | |
| 6,493,575 B1 | 12/2002 | Kesten | |
| 6,690,963 B2 | 2/2004 | Ben Haim | |
| 6,814,733 B2 | 11/2004 | Schwartz | |
| 6,892,091 B1 | 5/2005 | Ben Haim | |
| 6,997,924 B2 | 2/2006 | Schwartz | |
| 7,156,816 B2 | 1/2007 | Schwartz | |
| 7,536,218 B2 | 5/2009 | Govari et al. | |
| 7,756,576 B2 | 7/2010 | Levin | |
| 8,303,505 B2 | 11/2012 | Webler et al. | |
| 8,456,182 B2 | 6/2013 | Bar-Tal et al. | |
| 8,478,383 B2 | 7/2013 | Bar-Tal et al. | |
| 2004/0097805 A1 | 5/2004 | Verard | |
| 2005/0024043 A1 | 2/2005 | Govari | |
| 2007/0270692 A1 | 11/2007 | Barbu | |
| 2007/0276227 A1* | 11/2007 | Boese | A61B 5/06 600/424 |
| 2008/0091171 A1 | 4/2008 | Strommer | |
| 2009/0076483 A1* | 3/2009 | Danehorn | A61M 25/01 604/528 |
| 2009/0135992 A1 | 5/2009 | Vaillant et al. | |
| 2009/0163800 A1 | 6/2009 | Xu | |
| 2010/0079158 A1* | 4/2010 | Bar-Tal | A61B 5/042 324/705 |
| 2010/0082280 A1 | 4/2010 | Schneider | |
| 2010/0256558 A1 | 10/2010 | Olson | |
| 2011/0013816 A1 | 1/2011 | Gogin | |
| 2011/0069063 A1 | 3/2011 | Liao | |
| 2012/0075638 A1 | 3/2012 | Rollins | |
| 2012/0165656 A1 | 6/2012 | Montag et al. | |
| 2012/0172712 A1 | 7/2012 | Bar-Tal | |
| 2012/0232384 A1 | 9/2012 | Wu et al. | |
| 2013/0072787 A1* | 3/2013 | Wallace | A61B 6/12 600/424 |
| 2013/0072788 A1 | 3/2013 | Wu | |
| 2013/0184569 A1 | 7/2013 | Strommer | |
| 2013/0231556 A1 | 9/2013 | Holsing et al. | |
| 2013/0301897 A1 | 11/2013 | Zhu | |
| 2013/0324833 A1 | 12/2013 | Barley | |
| 2013/0331687 A1 | 12/2013 | Liao | |
| 2014/0016851 A1 | 1/2014 | Nakano | |
| 2014/0031676 A1 | 1/2014 | Nempont | |
| 2014/0142419 A1* | 5/2014 | Shalgi | A61B 6/503 600/424 |
| 2014/0221803 A1* | 8/2014 | Bar-Tal | A61B 5/063 600/373 |
| 2015/0238159 A1 | 8/2015 | Al Assad | |
| 2015/0313563 A1 | 11/2015 | Kelm | |
| 2016/0157751 A1 | 6/2016 | Mahfouz | |

FOREIGN PATENT DOCUMENTS

| | | |
|---|---|---|
| EP | 2732765 | 8/2014 |
| WO | WO 96/05768 A1 | 2/1996 |
| WO | WO 2007/138492 | 12/2007 |
| WO | WO 2013/036831 | 3/2013 |
| WO | WO 2013/057641 | 4/2013 |
| WO | WO 2014/124447 | 8/2014 |

OTHER PUBLICATIONS

Lindell, I.V. et al., Magnetostratic Image Theory for the Premeable Sphere, IEEE Transactions on Magnetics, (Jul. 1992) vol. 28, No. 4, pp. 1930-1934.
Co-pending U.S. Appl. No. 14/140,112, filed Dec. 24, 2013.
Felsberg, M. et al. The Monogenic Signal, IEEE Transactions on Signal Processing. vol. 49, No. 12, Dec. 2011, pp. 3136-3144.
Landau, L.D. et al. Electrodynamics of Continuous Media. Pergamon Press, 1960, vol. 8 of Course of Theoretical Physics, Textbook: ISBN No. 0-08-09105-9.
Loy, G. et al. A Fast Radial Symmetry Transform for Detecting Points of Interest. IEEE Transactions on Pattern Analysis and Machine Intelligence, Australian National University, Aug. 2003.
Extended European Search Report for EP16155496.9 Application, dated Jul. 6, 2016.
Extended European Search Report for EP16155431.6 Application, dated Jun. 29, 2016.

* cited by examiner

TRAINING OF IMPEDANCE BASED LOCATION SYSTEM USING REGISTERED CATHETER IMAGES

CROSS-REFERENCE TO RELATED APPLICATION

This application is related to U.S. Patent Application titled "Compensation for Heart Movement using Coronary Sinus Catheter Images" filed on even date with the present application, and which is incorporated herein by reference.

FIELD OF THE INVENTION

The present invention relates generally to tracking of a probe, and specifically to tracking of a catheter probe within a body organ.

BACKGROUND OF THE INVENTION

Tracking of the location of catheters within the human body is necessary in much of the surgery performed today. In addition to providing the position of the catheter itself, the tracking may also be used to provide other information such as the shape of an organ within which the catheter is located, by touching the surface of the organ. If the catheter is inserted into an organ in such a way so as not to move within the organ, movement of the organ as a whole may be determined by tracking the location of the catheter.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

inserting a catheter having at least one electrode into a chamber of a body organ of a patient;

recording at a sequence of times respective sets of currents between the at least one electrode and a plurality of patches positioned on skin of the patient;

while recording the sets of currents, acquiring x-ray images of the at least one electrode, and determining locations of the catheter from the images;

deriving a relation between the locations and the respective sets of currents based on the sets of currents and the images;

recording subsequent sets of currents between the at least one electrode and the patches; and determining, based on the relation, subsequent locations of the catheter in response to the subsequent set of currents.

Typically the body organ includes a heart of the patient, and the chamber is a coronary sinus of the heart.

In a disclosed embodiment no x-ray images are acquired while recording the subsequent sets of currents.

In a further disclosed embodiment the method includes analyzing the x-ray images to identify phases in a respiration cycle of the patient, and the relation includes multiple relations respectively based on the phases.

In a yet further disclosed embodiment the method includes analyzing the sets of currents to identify phases in a respiration cycle of the patient, and the relation includes multiple relations respectively based on the phases.

The body organ may be a heart, and the method may further include acquiring electrocardiograph (ECG) signals from the heart, analyzing the signals to identify phases in a heartbeat cycle of the patient, and the relation may include multiple relations respectively based on the phases. Alternatively or additionally the relation may include an average of multiple relations respectively based on the phases.

In an alternative embodiment the method includes, after deriving the relation, inserting a further catheter having a further-catheter-at-least-one-electrode into a further chamber in proximity to the chamber of the body organ, recording further sets of currents between the further-catheter-at-least-one-electrode and the patches, and determining, based on the relation, locations of the further catheter in response to the further sets of currents.

In a further alternative embodiment the method includes, while recording the sets of currents, acquiring x-ray images of the plurality of patches, and determining the locations typically includes determining the locations of the catheter from the x-ray images of the plurality of patches and the at least one electrode.

There is further provided, according to an embodiment of the present invention a method, including:

inserting a first catheter having at least one electrode and at least one coil into a chamber of a body organ of a patient;

recording at a sequence of times respective sets of currents between the at least one electrode and a plurality of patches positioned on skin of the patient;

while recording the sets of currents, acquiring x-ray images of the at least one electrode and the plurality of patches, and determining locations of the catheter from the images;

while recording the sets of currents, recording signals generated in the at least one coil in response to magnetic fields irradiating the catheter, and determining measures of the locations in response to the signals;

deriving a relation between the locations and the sets of currents based on the sets of currents, the signals, and the images;

removing the first catheter and inserting a second catheter having a second-catheter-at-least-one-electrode and no coil into the body organ;

recording subsequent sets of currents between the second-catheter-at-least-one-electrode and the patches; and determining, based on the relation, subsequent locations of the second catheter in response to the subsequent set of currents.

There is further provided, according to an embodiment of the present invention, apparatus, including:

a catheter having at least one electrode which is configured to be inserted into a chamber of a body organ of a patient; and a processor, which is configured to:

record at a sequence of times respective sets of currents between the at least one electrode and a plurality of patches positioned on skin of the patient, while recording the sets of currents, acquire x-ray images of the at least one electrode and the plurality of patches, and determine locations of the catheter from the images, derive a relation between the locations and the respective sets of currents based on the sets of currents and the images, record subsequent sets of currents between the at least one electrode and the patches, and determine, based on the relation, subsequent locations of the catheter in response to the subsequent set of currents.

The present disclosure will be more fully understood from the following detailed description of the embodiments thereof, taken together with the drawings, in which:

DETAILED DESCRIPTION OF EMBODIMENTS

Overview

Figure 1:
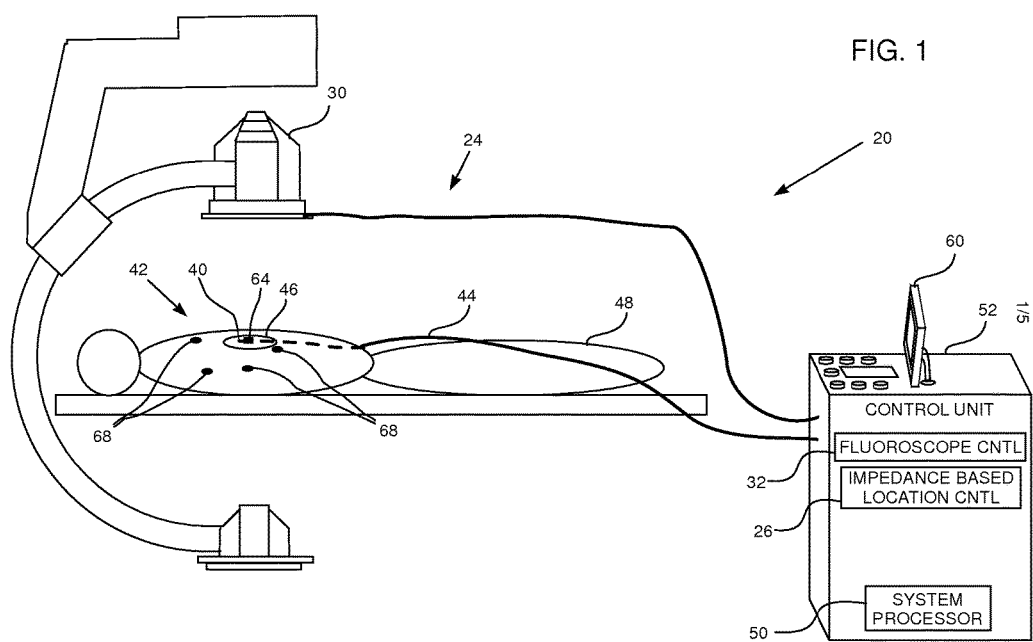
FIG. 1 is a schematic diagram illustrating a hybrid tracking system, according to an embodiment of the present invention.

An embodiment of the present invention provides a system for determining the location of a catheter, typically the distal tip of the catheter, which is inserted into the chamber of a body organ of a patient. The catheter has at least one electrode attached to its distal tip. Typically the chamber may be any cavity of the body organ into which it is possible to insert a catheter. In some embodiments the body organ is the heart of the patient, and in the following explanation the chamber is assumed to be the coronary sinus of the heart.

Electrode patches are attached to the skin of the patient, in the vicinity of the heart, and currents between the at least one electrode of the catheter and the patches are recorded. The currents are recorded over a sequence of times, generating respective sets of currents.

While the sets of currents are being recorded, in a training phase of the system, x-ray images of the at least one electrode and the plurality of patches are acquired, and locations of the catheter are determined from the images. A processor of the system derives a relation between the locations and the respective sets of currents based on the sets of currents and the images.

In an operational phase of the system, subsequent sets of currents between the at least one electrode and the patches are recorded, while no x-ray images are acquired. In the operational phase, subsequent locations of the catheter are determined in response to the subsequent set of currents.

In embodiments of the present invention the at least one electrode of the catheter may be the only means, incorporated into the catheter, that enable the locations of the catheter to be determined. The relation between the sets of currents and catheter locations (found from x-ray images) determined in a training phase provides a very good method for accurately determining, from subsequent sets of currents in an operational phase, subsequent locations of the catheter, notwithstanding that the catheter has no other means for determining its location.

DETAILED DESCRIPTION

In the following description, like elements in the drawings are identified by like numerals, and the like elements are differentiated as necessary by appending a letter to the identifying numeral.

FIG. 1 is a schematic diagram illustrating a hybrid tracking system 20, according to an embodiment of the present invention.

System 20 comprises an impedance based location facility 24, which is described in more detail below and which is operated by an impedance based location controller 26. System 20 also comprises fluoroscopic equipment 30, operated by a fluoroscope controller 32. While FIG. 1 shows, by way of example and for simplicity, equipment 30 as comprising a "C-arm" fluoroscope, the fluoroscopic equipment may comprise any fluoroscope known in the art, and/or computerized tomography (CT) x-ray equipment, that is able to generate fluoroscopic images.

As is explained in more detail below, in an initial "training" session of system 20 both the impedance based location facility and the fluoroscopic equipment operate. In a subsequent operational session of the system only the impedance based location facility is required to operate. In the operational phase the system determines a location of a distal tip 40 of a catheter 44 in a chamber 42 of a body organ 46 of a patient 48. The determination uses currents from an electrode 64 on the distal tip, as is described in more detail below.

In the present disclosure and in the claims, reference to a chamber of a body organ is to be understood as reference to any cavity of a body organ into which the distal tip of a catheter may be inserted. By way of example, and for clarity, in the following description body organ 46 is assumed to be the heart of patient 48, and the body organ is also referred to herein as heart 46. Also by way of example and for clarity in the following description chamber 42 is assumed to be the coronary sinus of heart 46, and the chamber is also referred to herein as coronary sinus 42. Those having ordinary skill in the art will be able to adapt the description, mutatis mutandis, for other body organs and for other chambers, such as, for the case of the heart, the left and right atria, and the left and right ventricles.

Figure 2A:
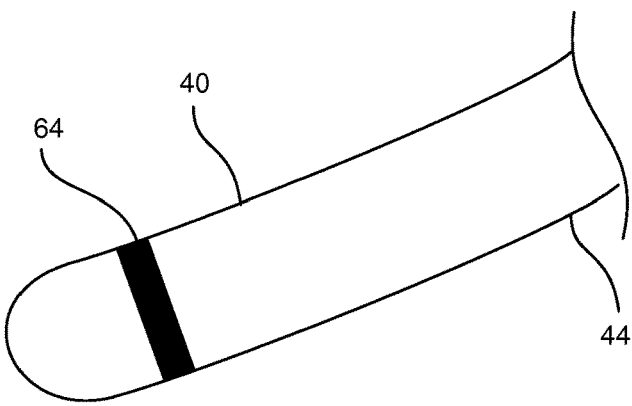
FIG. 2A is a schematic illustration of a distal tip of a catheter.
Figure 2B:
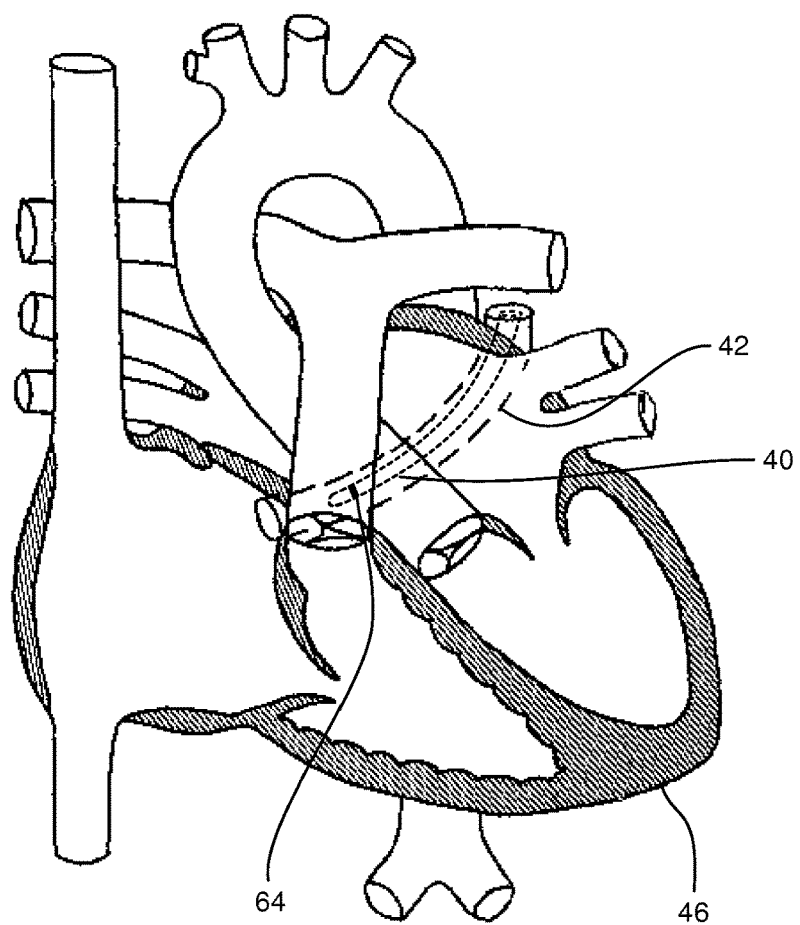
FIG. 2B is a schematic illustration of the distal tip inserted into a heart, according to embodiments of the present invention.

FIG. 2A is a schematic illustration of distal tip 40, and FIG. 2B is a schematic illustration of the distal tip inserted into heart 46, according to embodiments of the present invention. The figures illustrate distal tip 40 after it has been inserted into coronary sinus 42.

System 20 is operated by a system processor 50, which uses software to integrate data and images provided by controllers 26 and 32. System processor 50 and controllers 26 and 32 are typically incorporated into a control unit 52 of system 20. The processor determines the distal tip location, and typically incorporates the location into an image of the body organ that is presented to an operator of system 20 on a screen 60 coupled to the control unit. The software for the processor may be downloaded in electronic form, over a network, for example, or it may, alternatively or additionally, be provided and/or stored on non-transitory tangible media, such as magnetic, optical, or electronic memory.

Controller 26 of the impedance based location facility measures currents between an electrode 64, in the catheter distal tip, and a plurality of generally similar patch electrodes 68, also herein termed patches, which are positioned on the skin of patient 48 in the vicinity of heart 46. (For clarity, connections between control unit 52 and patches 68 are not shown in FIG. 1.) The currents between electrode 64 and the patches vary according to the location of the electrode, because of the different distances of the distal tip from the patches, which cause different impedances between the distal tip electrode and the different patches. Controller 26 is configured to generate an indication of the location from the different currents. Operational details of a facility similar to facility 24 are described in U.S. Pat. No. 8,456,182 to Bar-Tal et al., which is assigned to the assignee of the present application and which is incorporated herein by reference.

The impedances between the distal tip electrode and the patches, as well as impedances between the patches, vary with the respiration cycle of patient 48, and so vary with time. Controller 26 is also configured to analyze the impedances, and to derive from the analysis of sets of impedances measured at respective times an indication of impedance sets corresponding to end-expirium points of the patient's respiration cycle. The analysis may also reference respective phases of other impedance sets in the cycle to the end-expirium point. Aspects of a system for analyzing respiration using impedances, similar to the analysis referred to above, are described in U.S. Patent Application 2012/0172712 to Bar-Tal, which is assigned to the assignee of the present application and which is incorporated herein by reference.

By virtue of being positioned on the skin of patient 48 in the vicinity of heart 46, patches 68 also receive electrocardiograph (ECG) signals generated by the heart, as the heart beats. Controller 26 is further configured to acquire the ECG signals, and to use the acquired signals as fiducials for referencing impedance sets acquired at respective times to phases in the heartbeat cycle of the patient.

Fluoroscopic controller 32 of equipment 30 acquires images of patient 48, including images of heart 46, electrode 64, and, in some embodiments, patches 68. From the images, fluoroscope controller 32 is able to estimate respective locations for the heart and the electrode in a fluoroscope frame of reference. Where the patches are imaged the controller may be able to estimate locations for the patches in the fluoroscope frame of reference. If equipment 30 comprises CT equipment, the CT images typically incorporate sufficient three-dimensional information so that controller 32 is able to analyze the images to derive the locations. If equipment 30 does not comprise CT equipment, the locations may be derived by analysis of images acquired when the equipment is in two or more orientations. U.S. Patent Application entitled Compensation for Heart Movement using Coronary Sinus Catheter Images, referenced above, describes a system for locating a coronary sinus catheter using fluoroscopy images generated from a fluoroscope in multiple orientations.

Patches 68 move with the respiration of the patient and so the patch locations vary with time. In embodiments where the patch location may be determined from the fluoroscope image, by analyzing, for each fluoroscopic image, sets of locations of patches 68 acquired at respective times, controller 32 is able to identify sets of patch locations (i.e., sets of images) corresponding to the end-expirium point in the respiration cycle of the patient. The controller may also reference respective phases of other patch location sets in the cycle to the end-expirium point. The identification of the phase in the respiration cycle, and of the end-expirium point, may be made independently of the identifications performed using the impedance based location facility.

Figure 3:
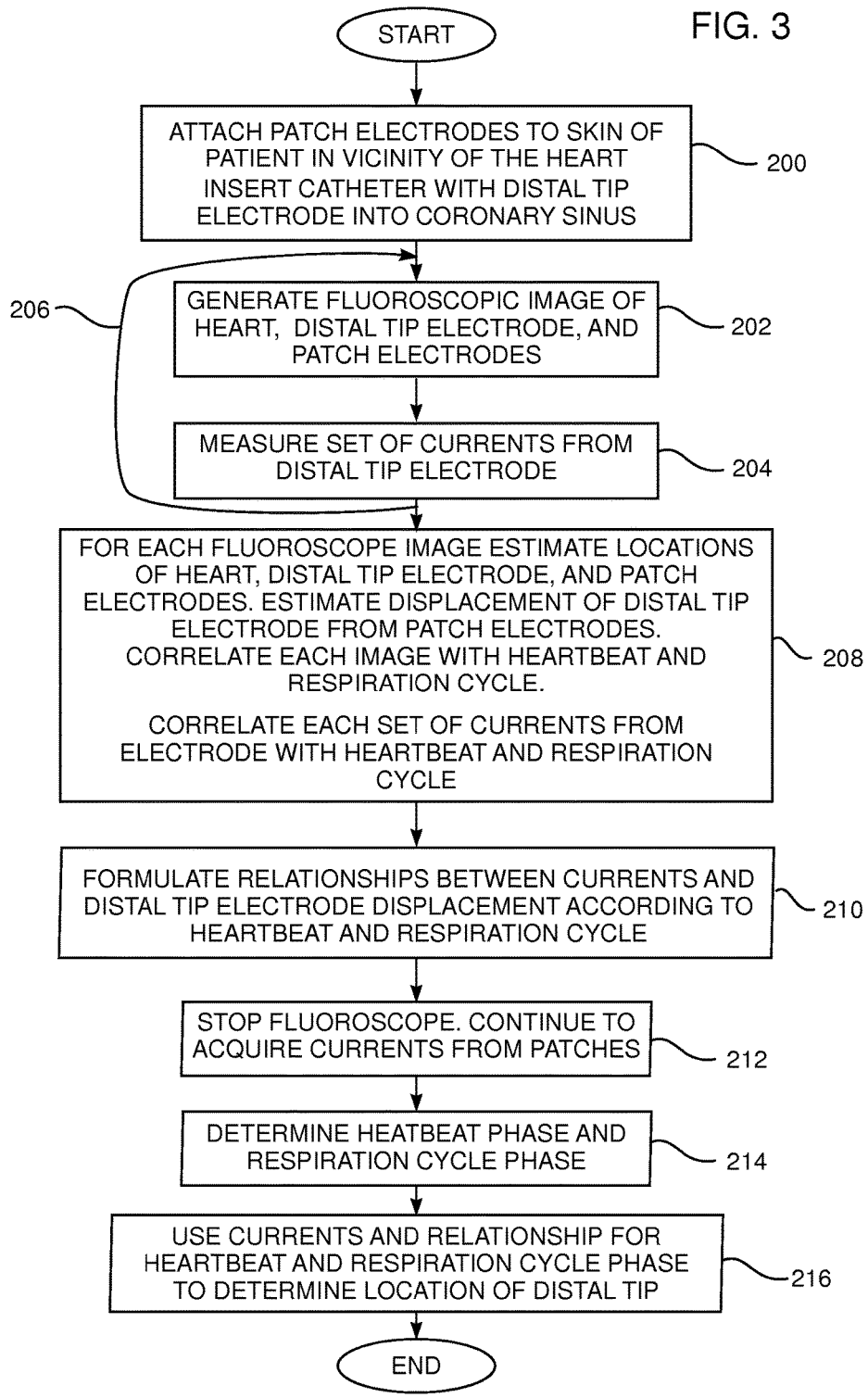
FIG. 3 is a flowchart of steps performed in operating the system of FIG. 1, according to an embodiment of the present invention.

FIG. 3 is a flowchart of steps performed in operating system 20, according to an embodiment of the present invention. In an initial step 200 of the flowchart, patches 68 are attached to the skin of patient 48, in the vicinity of heart 46, and the patches are connected with conducting cables to control unit 52. In addition, distal tip 40 of the catheter is inserted into coronary sinus 42.

In a fluoroscopic imaging step 202, which begins a training phase of the flowchart, fluoroscope controller 32 operates equipment 30, so that the controller acquires an x-ray image of patient 48, including within the image respective sub-images of heart 46, distal tip electrode 64, and patches 68.

In a current measurement step 204, which is typically performed substantially simultaneously with imaging step 202, impedance based controller 26 records respective "training" currents between each patch 68 and distal tip electrode 64, as a set of currents $\{I_T\}$.

As indicated by an arrow 206, steps 202 and 204 are repeated on a continuing basis, typically for a period of approximately 10 s, although the period of repetition may be longer or smaller than 10 s. In order to accommodate movements of the distal tip and of the patches because of the breathing of the patient, as well as because of the beating of the patient's heart, the respective controllers record times for each of the steps.

In an analysis step 208, the fluoroscope controller analyzes the sub-images in each of the images acquired in steps 202 so as to determine, within a fluoroscopy frame of reference defined by equipment 30, estimates of the respective locations of heart 46, distal tip electrode 64, and each of patches 68. By comparing the locations of the patches the fluoroscope controller registers successive images with the respiration cycle of patient 48, and identifies images corresponding to end-expirium points and to other phases in the cycle.

From the estimated locations of the electrode and the patches, the controller generates, for each image, a set of "training" displacement vectors $\{D_T\}$ representative of the displacement of the distal tip electrode from each of patches 68. Each set of vectors $\{D_T\}$ is further categorized according to its corresponding phases in the patient's respiration cycle and heartbeat (the latter determined from the ECG signals), so that the fluoroscope controller generates sets of vectors $\{D_T\}_H^R$, where R is an index representative of the phase of respiration cycle, and H is an index representative of the phase of the heartbeat.

Also in the analysis step, the impedance based controller categorizes each set of currents $[I_T]$ acquired in step 204 according to the phases of the patient's respiration cycle and heartbeat, so generating sets of current vectors $\{[I_T]\}_H^R$.

In a relationship step 210, the system processor finds and stores matrices $M_H^R$ forming a relation between the sets of displacement vectors $\{D_T\}_H^R$ and the sets of current vectors $\{[I_T]\}_H^R$, according to equation (1):

$$\{D_T\}_H^R = M_H^R \cdot \{[I_T]\}_H^R \tag{1}$$

Steps 202-210 comprise a training phase of the flowchart, and storing of matrices $M_H^R$ in step 210 corresponds to the termination of the training phase.

In an initial step 212 of an operational phase of the flowchart, the fluoroscope equipment is powered off. Catheter 44 may be left in place in coronary sinus 42, or alternatively the catheter may be replaced at a later time in the coronary sinus by another, similar, catheter, which is tracked as described below. While the fluoroscope equipment is no longer operative, the impedance based location facility continues to operate. During its operation impedance based controller 26 acquires sets of operational current vectors $[I_O]$ from patches 68, and also continues to receive ECG signals.

In an operational analysis step 214, performed for each set of current vectors $[I_O]$ acquired in step 212, controller 26 analyses the set of vectors to determine the phase of the respiration cycle R, and also analyses the ECG signals to determine the phase of the patient's heartbeat H. Each set of current vectors may thus be designated as $[I_O]_H^R$.

In a distal tip location step 216, the matrix $M_H^R$ for the values of R and H determined in step 214 is retrieved, and is used to determine a set of displacement vectors $\{D_O\}_H^R$ for the distal tip, according to equation (2):

$$\{D_O\}_H^R = M_H^R \cdot \{[I_O]\}_H^R \qquad (2)$$

The displacement vectors determined from equation (2) for the distal tip may be used directly as indicators of the heart location, if the distal tip is in the coronary sinus, since there is relatively little movement, i.e., change of displacement, between the coronary sinus and the rest of the heart. Alternatively, movement between the distal tip (in the coronary sinus) and the heart may be accounted for using the estimates of the heart location and the distal tip electrode generated in step 208; in some embodiments adjustments for the movement are gated to the heartbeat and/or the respiration cycle of the patient, substantially as described above for the distal tip displacement vectors.

In some embodiments, rather than measuring and/or gating data according to heartbeat phase index H, the data is averaged over a complete heartbeat. Those having ordinary skill in the art will be able to adapt the description, mutatis mutandis, for the case where such an average of the data is derived.

The description above assumes that catheter 44, or a replacement, is in coronary sinus 42 after the training phase of system 20, so that catheter 44 or its replacement is tracked in the operational phase. In alternative embodiments, an alternative catheter similar to catheter 44, i.e. a catheter having an electrode but no coils (such coils are described below with reference to FIGS. 4 and 5) is positioned in a chamber in proximity to the coronary sinus, used during the training phase of catheter 44. For example the alternative catheter may be positioned in the right ventricle of heart 46. Sets of current vectors for the alternative catheter are acquired, as described above for step 212, and equation (2) is used to derive displacement vectors for the alternative catheter.

Figure 4:
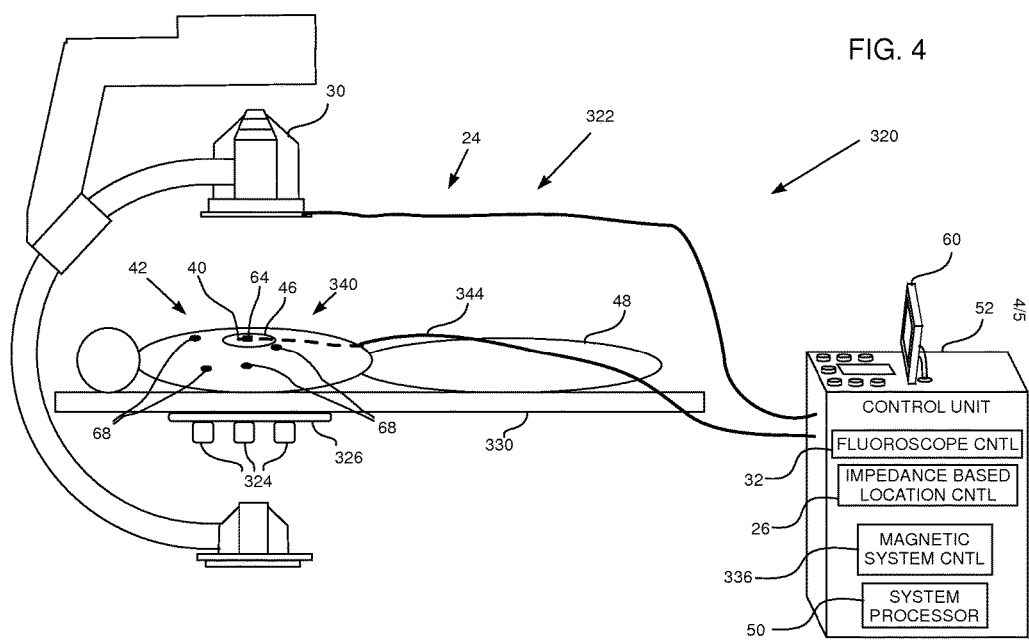
FIG. 4 is a schematic diagram illustrating a hybrid tracking system, according to an alternative embodiment of the present invention.

FIG. 4 is a schematic diagram illustrating a hybrid tracking system 320, according to an alternative embodiment of the present invention. Apart from the differences described below, the operation of system 320 is generally similar to that of system 20 (FIGS. 1-3), and elements indicated by the same reference numerals in both systems 20 and 320 are generally similar in construction and in operation.

System 320 comprises a magnetic tracking system 322 which typically has three sets 324 of generally similar coils fixedly mounted on a location pad 326. Each set 324 of coils typically comprises three orthogonally oriented coils, so that there are a total of nine coils fixedly attached to pad 326. Pad 326 is fixedly attached to the underside of a table 330 upon which patient 48 is resting, and the coils, under control of a magnetic system controller 336, transmit alternating magnetic fields into a region 340 in proximity to heart 46. Rather than using catheter 44, system 320 uses a catheter 344.

Figure 5:
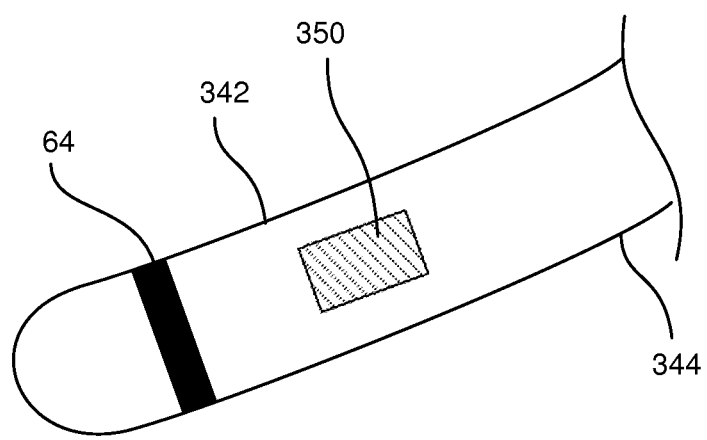
FIG. 5 is a schematic diagram illustrating a distal tip of a catheter used in the system of FIG. 4, according to an alternative embodiment of the present invention.

FIG. 5 is a schematic diagram illustrating a distal tip 342 of catheter 344, according to an alternative embodiment of the present invention. Distal tip 342 is generally similar to distal tip 40 of catheter 44, having electrode 64 on the surface of the distal tip. In addition, tip 342 comprises one or more coils 350 within the tip.

The one or more catheter coils 350 generate signals in response to the magnetic fields (from sets 324) received by the coils, and controller 336 acquires the signals from coils 350, and processes the signals in order to determine a location of the catheter coils with respect to location pad 326. Patches 68 also have coils incorporated into the patches, and controller 336 is able to process signals from the coils to determine locations of the patches with respect to the location pad. A system similar to magnetic tracking system 322 is the Carto™ system produced by Biosense Webster Inc., of Diamond Bar, Calif., and is also described in U.S. Pat. No 8,456,182 referenced above.

In an alternative embodiment of the present invention, hybrid tracking system 320 and catheter 344 is used in the training phase referred to above. However, in the operational phase, rather than catheter 344 being used, catheter 44, having no coils 350 in its distal end, is used. Except for the differences described below, the flowchart of FIG. 3 describes steps taken in operation of the alternative embodiment.

In step 208 of the training phase of the alternative embodiment, estimates of sets of displacement vectors of catheter distal tip 342 with respect to patches 68 may be made from only the fluoroscopic images, as is described above, or from only magnetic tracking system 322. In some embodiments both the fluoroscopic images and the magnetic tracking system are used to estimate the displacement vectors, typically by averaging the vectors determined by the fluoroscopic system with those determined from the magnetic tracking system. In the following description the estimates of analysis step 208 in the alternative embodiment are assumed to produce sets of displacement vectors $\{D'_T\}_H^R$.

In the alternative embodiment, sets $\{D'_T\}_H^R$ are used in relationship step 210 to find and store matrices $M'_H^R$, generated according to equation (3):

$$\{D'_T\}_H^R = M'_H^R \cdot \{[I_T]\}_H^R \qquad (3)$$

In the operational phase of the alternative embodiment, catheter 344 may be removed from coronary sinus 42, and catheter 44 may be placed into the coronary sinus or into another chamber of heart 46. Matrices $M'_H^R$ are used to determine a set of displacement vectors $\{D_O\}_H^R$ for the distal tip of catheter 44, according to equation (4):

$$\{D_O\}_H^R = M'_H^R \cdot \{[I_O]\}_H^R \qquad (4)$$

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
   inserting a catheter having at least one electrode including a distal tip electrode into a chamber of a body organ of a patient;
   during a predetermined period of time, repeatedly acquiring an x-ray image of the at least one electrode and a plurality of patches positioned on skin of the patient;

simultaneously with each x-ray image acquisition, recording a set of currents between the at least one electrode and the plurality of patches positioned on skin of the patient to thereby record a plurality of sets of currents;

determining locations of the catheter and locations of the plurality of patches from each one of the images;

determining a plurality of displacement vectors from the locations of the catheter and locations of the plurality of patches, each displacement vector being representative of the displacement of the distal tip electrode from the plurality of patches;

categorizing the plurality of displacement vectors and the plurality of sets of currents according to corresponding phases in the patient's respiration cycle and heartbeat; and deriving a matrix forming a relation between the locations of the catheter, locations of the patches and the plurality of sets of currents based on the categorized plurality of sets of currents and plurality of displacement vectors;

recording subsequent sets of currents between the at least one electrode and the patches; and determining, based on the relation, subsequent locations of the catheter in response to the subsequent set of currents.

2. The method according to claim 1, wherein the body organ comprises a heart of the patient, and wherein the chamber comprises a coronary sinus of the heart.

3. The method according to claim 1, wherein no x-ray images are acquired while recording the subsequent sets of currents.

4. The method according to claim 1, and comprising analyzing the x-ray images to identify phases in a respiration cycle of the patient, and wherein the relation comprises multiple relations respectively based on the phases.

5. The method according to claim 1, and comprising analyzing the sets of currents to identify phases in a respiration cycle of the patient, and wherein the relation comprises multiple relations respectively based on the phases.

6. The method according to claim 1, wherein the body organ comprises a heart, the method further comprising acquiring electrocardiograph (ECG) signals from the heart, analyzing the signals to identify phases in a heartbeat cycle of the patient, and wherein the relation comprises multiple relations respectively based on the phases.

7. The method according to claim 1, wherein the body organ comprises a heart, the method further comprising acquiring ECG signals from the heart, analyzing the signals to identify phases in a heartbeat cycle of the patient, and wherein the relation comprises an average of multiple relations respectively based on the phases.

8. The method according to claim 1, and comprising, after deriving the relation, inserting a further catheter having a further-catheter-at-least-one-electrode into a further chamber in proximity to the chamber of the body organ, recording further sets of currents between the further-catheter-at-least-one-electrode and the patches, and determining, based on the relation, locations of the further catheter in response to the further sets of currents.

9. The method according to claim 1, and comprising while recording the sets of currents, acquiring x-ray images of the plurality of patches, and wherein determining the locations comprises determining the locations of the catheter from the x-ray images of the plurality of patches and the at least one electrode.

10. A method, comprising:
inserting a first catheter having at least one electrode including a distal tip electrode and at least one coil into a chamber of a body organ of a patient;

during a predetermined period of time, repeatedly acquiring an x-ray image of the at least one electrode and a plurality of patches positioned on skin of the patient, and determining locations of the catheter and the plurality of patches from the images;

simultaneously with the acquisition of each x-ray image, recording set of currents between the at least one electrode and the plurality of patches positioned on skin of the patient to thereby record a plurality of sets of currents;

while recording each one of the plurality of sets of currents, recording signals generated in the at least one coil in response to magnetic fields irradiating the catheter, and determining measures of the locations in response to the signals;

determining a plurality of displacement vectors from the locations of the catheter and locations of the plurality of patches, each displacement vector being representative of the displacement of the distal tip electrode from the plurality of patches;

categorizing the plurality of displacement vectors and the plurality of sets of currents according to corresponding phases in the patient's respiration cycle and heartbeat; and deriving a matrix forming a relation between the locations and the plurality of sets of currents based on the categorized plurality of sets of currents and plurality of displacement vectors;

removing the first catheter and inserting a second catheter having a second-catheter-at-least-one-electrode and no coil into the body organ;

recording subsequent sets of currents between the second-catheter-at-least-one-electrode and the patches; and determining, based on the relation, subsequent locations of the second catheter in response to the subsequent set of currents.

11. Apparatus, comprising:
a catheter having at least one electrode including a distal tip electrode which is configured to be inserted into a chamber of a body organ of a patient; and a processor, which is configured to:

during a predetermined period of time, repeatedly acquire at least one x-ray image of the at least one electrode and a plurality of patches positioned on skin of the patient, and determine locations of the catheter and locations of the plurality of patches from each one of the images, simultaneously with the acquisition of each x-ray image, record set of currents between the at least one electrode and the plurality of patches to thereby record a plurality of sets of currents, determine a plurality of displacement vectors from the locations of the catheter and locations of the plurality of patches, each displacement vector being representative of the displacement of the distal tip electrode from the plurality of patches;

categorize the plurality of displacement vectors and the plurality of sets of currents according to corresponding phases in the patient's respiration cycle and heartbeat; and derive a matrix forming a relation between the locations of the catheter, locations of the plurality of patches and the plurality of sets of currents based on the categorized plurality of sets of currents and plurality of displacement vectors, record subsequent sets of currents between the at least one electrode and the patches, and determine, based on the relation, subsequent locations of the catheter in response to the subsequent set of currents.

12. The apparatus according to claim 11, wherein the body organ comprises a heart of the patient, and wherein the chamber comprises a coronary sinus of the heart.

13. The apparatus according to claim 11, wherein no x-ray images are acquired while recording the subsequent sets of currents.

14. The apparatus according to claim 11, wherein the processor is configured to analyze the x-ray images to identify phases in a respiration cycle of the patient, and wherein the relation comprises multiple relations respectively based on the phases.

15. The apparatus according to claim 11, wherein the processor is configured to analyze the sets of currents to identify phases in a respiration cycle of the patient, and wherein the relation comprises multiple relations respectively based on the phases.

16. The apparatus according to claim 11, wherein the body organ comprises a heart, wherein the processor is configured to acquire electrocardiograph (ECG) signals from the heart, analyze the signals to identify phases in a heartbeat cycle of the patient, and wherein the relation comprises multiple relations respectively based on the phases.

17. The apparatus according to claim 11, wherein the body organ comprises a heart, wherein the processor is configured to acquire ECG signals from the heart, analyze the signals to identify phases in a heartbeat cycle of the patient, and wherein the relation comprises an average of multiple relations respectively based on the phases.

18. The apparatus according to claim 11, and comprising a further catheter, having a further-catheter-at-least-one-electrode, which is configured to be inserted, after deriving the relation, into a further chamber in proximity to the chamber of the body organ, and wherein the processor is configured to record further sets of currents between the further-catheter-at-least-one-electrode and the patches, and determine, based on the relation, locations of the further catheter in response to the further sets of currents.

19. The apparatus according to claim 11, and comprising configuring the processor to, while recording the sets of currents, acquire x-ray images of the plurality of patches, and wherein determining the locations comprises determining the locations of the catheter from the x-ray images of the plurality of patches and the at least one electrode.

* * * * *